United States Patent [19]

Steckel

[11] Patent Number: 5,053,152
[45] Date of Patent: Oct. 1, 1991

[54] HIGH MOLECULAR WEIGHT NITROGEN-CONTAINING CONDENSATES AND FUELS AND LUBRICANTS CONTAINING SAME

[75] Inventor: Thomas F. Steckel, Chagrin Falls, Ohio

[73] Assignee: The Lubrizol Corporation, Wickliffe, Ohio

[21] Appl. No.: 390,439

[22] Filed: Aug. 3, 1989

Related U.S. Application Data

[63] Continuation of Ser. No. 711,799, Mar. 14, 1985, abandoned.

[51] Int. Cl.$^5$ .............................. C10M 149/22
[52] U.S. Cl. ...................... 252/51.5 R; 252/50; 564/479; 564/505; 564/512
[58] Field of Search ............ 564/479, 505, 512; 252/47.5, 50, 51.5 R

[56] References Cited

U.S. PATENT DOCUMENTS

| | | | |
|---|---|---|---|
| 3,200,106 | 8/1965 | Dickson et al. | 564/505 |
| 3,219,666 | 11/1965 | Normal et al. | 260/268 |
| 3,272,746 | 9/1966 | Le Suer et al. | 252/47.5 |
| 3,700,598 | 10/1972 | Plonsker et al. | 564/512 |
| 3,948,800 | 4/1976 | Meinhardt | 252/356 |
| 4,116,643 | 9/1978 | Ryer et al. | 44/63 |
| 4,200,545 | 4/1980 | Clason | 252/33.4 |
| 4,234,435 | 11/1980 | Meinhardt et al. | 252/51.5 A |
| 4,394,524 | 7/1983 | Ford et al. | 564/479 |
| 4,428,849 | 1/1984 | Wistosky | 252/33.4 |
| 4,454,059 | 6/1984 | Pindar et al. | 252/51.5 R |
| 4,477,362 | 10/1984 | Steckel | 252/51.5 |
| 4,503,253 | 3/1985 | Ford et al. | 564/479 |
| 4,631,337 | 12/1986 | Tomalia et al. | 564/512 |
| 4,888,425 | 12/1989 | Herdle | 564/479 |

FOREIGN PATENT DOCUMENTS 882024 9/1971 Canada.
1069136 1/1980 Fed. Rep. of Germany.

OTHER PUBLICATIONS

Encyclopedia of Polymer Science and Technology, vol. 10, p. 621 (1969).
Encyclopedia of Polymer Science and Engineering, vol. 1, pp. 695, 723 (year unknown).
Chemical Abstracts, 85:126891q (1976).
Chemical Abstracts, 85:126893s (1976).
Chemical Abstracts, 85:126897w (1976).
Chemical Abstracts, 85:145575f (1976).
Chemical Abstracts, 85:145576g (1976).
Chemical Abstracts, 85:179986f (1976).
Chemical Abstracts, 85:179988h (1976).
Chemical Abstracts, 85:179990c (1976).
Chemical Abstracts, 86:7041y (1977).
Chemical Abstracts, 86:7043a (1977).
Chemical Abstracts, 86:7044b (1977).
Chemical Abstracts, 86:7047e (1977).
Chemical Abstracts, 86:31766j (1977).
Chemical Abstracts, 87:25813b (1977).
Chemical Abstracts, 87:25823e (1977).
Chemical Abstracts, 87:25824f (1977).
Chemical Abstracts, 87:25829m (1977).
Chemical Abstracts, 87:26821q (1977).
Chemical Abstracts, 87:70791d (1977).
Chemical Abstracts, 87:70793f (1977).
Chemical Abstracts, 87:70796j (1977).
Chemical Abstracts, 87:70798m (1977).
Chemical Abstracts, 88:39670k (1978).
Chemical Abstracts, 89:113753d (1978).
Chemical Abstracts, 89:113755f (1978).
Chemical Abstracts, 89:113758j (1978).
Chemical Abstracts, 89:113763g (1978).
Chemical Abstracts, 89:113780k (1978).
Chemical Abstracts, 89:113782n (1978).
Chemical Abstracts, 89:113790p (1978).
Chemical Abstracts, 89:165949s (1978).
Chemical Abstracts, 89:113794t (1978).
Chemical Abstracts, 89:165969y (1978).
Chemical Abstracts, 89:165970s (1978).
Chemical Abstracts, 89:165972u (1978).

*Primary Examiner*—Prince E. Willis
*Assistant Examiner*—Ellen McAvoy
*Attorney, Agent, or Firm*—Joseph P. Fischer; Frederick D. Hunter; James L. Cordek

[57] ABSTRACT

Improved additives/dispersants for lubricant and fuel compositions are obtained by condensing a hydroxyalkyl or hydroxyaryl compound with an amine compound. The condensates according to the present invention are produced by the acid catalyzed condensation of the amine reactant with the hydroxy reactant.

40 Claims, No Drawings

HIGH MOLECULAR WEIGHT NITROGEN-CONTAINING CONDENSATES AND FUELS AND LUBRICANTS CONTAINING SAME

This is a continuation of co-pending application Ser. No. 07/711,799 filed on Mar. 14, 1985, now abandoned.

BACKGROUND

1. Field of the Invention

This invention relates to a high molecular weight N-containing condensate useful in lubricant and fuel compositions. More specifically, this invention relates to an additive and a dispersing aid for lubricants and fuel compositions, including dispersants that exhibit a high total base number and contain a low free amine content. The condensates of the present invention are produced by the acid catalyzed condensation of an amine reactant with a hydroxy alkyl or hydroxy aryl reactant.

2. State of the Art

Nitrogen containing dispersing aids for lubricants and fuel compositions are known and widely used in this technology. For example, in U.S. Pat. Nos. 3,219,666 and 3,272,746 various nitrogen containing "ashless" type dispersing agents for lubricants and fuel compositions are disclosed.

In U.S. Pat. No. 4,428,849 an alkenyl succinimide or borated alkenyl succinimide is reacted with an alkylene polyamine to produce a dispersant for lubricant oil useful for diesel engines.

U.S. Pat. No. 4,234,435, discloses various carboxylic acid acylating agents which can be further reacted with such reactants as polyethylene polyamines and polyols to produce derivatives useful as lubricant additives or as intermediates for further post treatment which find other uses in the lubricant additive technology.

U.S. Pat. No. 4,477,362 discloses various nitrogen- and oxygen- containing compositions which are prepared by reacting an aliphatic hydroxy compound with at least one tertiary amino alkanol to produce derivatives useful as lubricant and fuel additives.

U.S. Pat. No. 4,200,545 describes various amino phenols which may be combined with a hydrocarbyl amine or acylated nitrogen containing, compound which resultant composition finds use as additives for fuels and lubricants to be added to 2-cycle engines.

U.S. Pat. No. 116,643 discloses amine salts of carboxylate half esters which are the reaction products of organic acid materials and hydroxy amines which materials find use as anti-rust additives for hydrocarbon fuels, such as gasoline and middle distillates.

None of the above-discussed patents disclose nor suggest the high molecular weight nitrogen-containing condensates of the present invention, i.e., condensing a high molecular weight polyamine reactant with a hydroxy alkyl or hydroxy aryl reactant.

SUMMARY OF THE INVENTION

In accordance with the present invention, a novel, high molecular weight extended polyamine has been discovered which has a viscosity greater than the viscosity of the amine reactant. The viscosity of the polyamine condensate, according to the present invention, may range up to the production of solid material depending upon the reaction conditions and the desired properties of the final product.

Further, in accordance with the invention, it has been found that the extended polyamines of the present invention are useful in the preparation of dispersants having substantially no free amine and improve the performance of lubricant and fuel compositions.

Still further, in accordance with the invention, it has been found that polyamines of the present invention may be used alone as dispersants and additives for lubricant and fuel compositions or may be further reacted with, for example, an acylating agent, to give an even higher molecular weight dispersant.

Still further, in accordance with the invention, a high yield, single step reaction comprising the dehydration condensation of at least one polyamine reactant with at least one hydroxy alkyl or hydroxy aryl reactant in the presence of an acid catalyst has been developed for the preparation of the high molecular polyamines of the present invention.

Still further, in accordance with the invention, various lubricant compositions, fuel compositions and other such functional fluid compositions comprising the high molecular weight extended polyamines or the reaction products thereof according to the present invention are contemplated and within the scope of the invention.

These and other aspects of the invention will become clear to those skilled in the art upon the reading and understanding of the specification.

DETAILED DESCRIPTION OF THE INVENTION

A novel class of high molecular weight polyamines has surprisingly been discovered and are illustrated by the following formula:

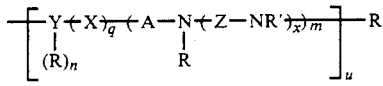

wherein R is independently hydrogen or hydrocarbyl, R' is hydrogen, alkyl or $NH_2R''[NR'']_y$ wherein y ranges from 1 to about 6 and R'' is an alkylene group of 1 to about 10 carbon atoms, X is an alkylene group of at least 1 carbon atom, Y represents sulfur, nitrogen, or oxygen, A is hydrocarbyl, Z is alkylene of 1 to about 10 carbon atoms, oxyalkylene of 1 to about 10 carbon atoms or a heterocyclic ring containing at least one nitrogen atom, and wherein n is 0 or 1 dependent upon m and q, q is 0 or 1, m is 1, 2 or 3, x is 1 to about 10 and u is a whole integer greater than one.

In a preferred embodiment, X and Z combined must consist of at least 2 carbon atoms. In one embodiment, the polyamine units according to the above formula (I) may be defined by the formula:

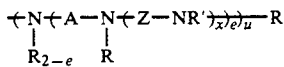

wherein R, R', A, Z, x and u are the same defined in formula (I) and e is 1 or 2.

The above described polyamines, as illustrated by Formula (I), are derived from:

(A) an hydroxy alkyl or hydroxy aryl reactant represented by formula (II) below:

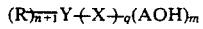     (II)

wherein R, Y, X, A, n, q and m are the same as defined hereinabove, and (B) a polyamine reactant illustrated by the formula (III) below:

wherein R, R', Z and x are the same as defined hereinabove.

As used herein, the term "hydrocarbyl" denotes a radical having a carbon atom directly attached to the remainder of the molecule and having predominantly hydrocarbon character within the context of this invention. Such radicals include the following:

(1) Hydrocarbon radicals; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, any two indicated substituents may together form an alicyclic radical). Such radicals are known to those skilled in the art; examples are (2) Substituted hydrocarbon radicals; that is, radicals containing non-hydrocarbon substituents which, in the context of this invention, do not alter the predominantly hydrocarbon character of the radical. Those skilled in the art will be aware of suitable substituents; examples are (3) Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbyl radical.

Terms such as "alkyl-based radical", "aryl-based radical" and the like have meaning analogous to the above with respect to alkyl and aryl radicals and the like.

Preferably, the hydrocarbyl radicals in the compounds of this invention are free from acetylenic and usually also from ethylenic unsaturation and have about at least one carbon atom. The radicals are usually hydrocarbon and especially lower hydrocarbon, the word "lower" denoting radicals containing up to seven carbon atoms. They are preferably lower alkyl or aryl radicals, most often alkyl.

The novel polyamine condensates of the present invention are prepared by the acid catalyzed condensation reaction of the hydroxy alkyl or hydroxy aryl reactant (II) with the amine reactant (III) at an elevated temperature.

The amine reactants, as represented by Formula (III) above, are characterized by the presence within their structure of the R-N group wherein R is described hereinabove and are lower molecular weight polyamines. Mixtures of two or more amines can be used in the reaction with one or more hydroxy alkyl or hydroxy aryl reactants which are within the scope of this invention. The amine reactants of the present invention may contain aliphatic, cycloaliphatic, aromatic, or heterocyclic, including aliphatic-substituted aromatic, aliphatic-substituted heterocyclic, cycloaliphatic substituted aliphatic, cycloaliphatic-substituted aromatic, cycloaliphatic-substituted heterocyclic, aromatic-substituted aliphatic, aromatic-substituted cycloaliphatic, aromatic-substituted heterocyclic, heterocyclic-substituted aliphatic, hetero-cyclic-substituted alicyclic, and heterocyclic-substituted aromatic groups and may contain unsaturated sites in the molecule. If the amine contains such unsaturated sites, such unsaturation will not be acetylenic. These amines may also contain non-hydrocarbon substituents or groups as long as these groups do not significantly interfere with the reaction of the amines with the hydroxy alkyl or hydroxy aryl reactants of the invention. Such non-hydrocarbon substituents or groups include lower alkoxy, lower alkyl mercapto, nitro, interrupting groups such as —O—and —S—(e.g., as in such groups as —CH$_2$CH$_2$—X—CH$_2$CH$_2$—where X is —O—or —S—).

Examples of suitable polyamine reactants according to the present invention include N-amino-propyl-cyclohexylamines, N-N'-di-n-butyl-para-phenylene diamine, bis-(para aminophenyl)methane, 1,4-diaminocyclohexane, and the like.

Heterocyclic polyamines can also be used as (III) in preparing the compositions of this invention. As used herein, the terminology "heterocyclic polyamine(s)" is intended to describe those heterocyclic amines containing at least one nitrogen as a hetero atom in the heterocyclic ring. The heterocyclic amines (according to the present invention) can be saturated or unsaturated and can contain various substituents such as nitro, alkoxy, alkyl mercapto, alkyl, alkenyl, aryl, alkaryl, or aralkyl substituents. Generally, the, total number of carbon atoms in the substituents will not exceed about 20. Heterocyclic amines can contain more than one nitrogen hetero atom. The 5- and 6-membered heterocyclic rings are preferred.

Among the suitable heterocyclic polyamines are aziridines, azetidines, azolidines, tetra- and di-hydro pyridines, pyrroles, indoles, piperidines, imidazoles, di-and tetra-hydroimidazoles, piperazines, isoindoles, purines, morpholines, thiomorpholines, N-aminoalkyl-morpholines N-aminoalkylthiomorpholines, N-aminoalkyl-piperazines, N,N'-di-aminoalkylpiperazines, azepines, azocines, azonines, azecines and tetra-, di- and perhydro derivatives of each of the above and mixtures of two or more of these heterocyclic amines. Preferred heterocyclic amines are the saturated 5- and 6-membered heterocyclic amines containing only nitrogen, oxygen and/or sulfur in the hetero ring, especially the piperidines, piperazines, thiomorpholines, morpholines, pyrrolidines, and the like. Piperidine, aminoalkyl-substituted piperidines, piperazine, aminoalkyl-substituted piperazines, morpholine, aminoalkyl-substituted morpholines, pyrrolidine, and aminoalkyl-substituted pyrrolidines, are especially preferred. Usually the aminoalkyl substituents are substituted on a nitrogen atom forming part of the hetero ring. Specific examples of such heterocyclic amines include aminopropylmorpholine, aminoethylpiperazine, and N,N'-di-aminoethylpiperazine.

Also suitable as amines are the aminosulfonic acids and derivatives thereof corresponding to the general formula:

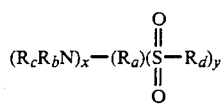 (IV)

wherein $R_d$ is $-NH_2$, alkali or alkaline earth metal, $R_a$ is a polyvalent organic radical having a valence equal to $x+y$; $R_b$ and $R_c$ are each independently hydrogen, hydrocarbyl, and substituted hydrocarbyl with the proviso that at least one of $R_b$ or $R_c$ is hydrogen per aminosulfonic acid molecule; x and y are each integers equal to or greater than one. From the formula, it is apparent that each amino sulfonic reactant is characterized by at least one HN or $H_2N-$group and at least one

group. These sulfonic acids can be aliphatic, cycloaliphatic, or aromatic aminosulfonic acids and the corresponding functional derivatives of the sulfo group. Specifically, the aminosulfonic acids can be aromatic aminosulfonic acids, that is, where $R_aY$ is a polyvalent aromatic radical such as phenylene where at least one

group is attached directly to a nuclear carbon atom of the aromatic radical. The aminosulfonic acid may also be a mono-amino aliphatic sulfonic acid; that is, an acid where x is one and $R_a$ is a polyvalent aliphatic radical such as ethylene, propylene, trimethylene, and 2-methylene propylene. Suitable aminosulfonic acids and derivatives thereof useful as the amine reactant (III) are disclosed in U.S. Pat. Nos. 3,029,250; 3,367,864; and 3,926,820; which are expressly incorporated herein by reference for such disclosure.

The high molecular weight hydrocarbyl polyamines, which can be used as III are generally prepared by reacting a chlorinated polyolefin having a molecular weight of at least about 400 with ammonia or the appropriate amine. Such amines are known in the art and described, for example, in U.S. Pat. Nos. 3,275,554 and 3,438,757, both of which are expressly incorporated herein by reference for their disclosure in regard to how to prepare these amines.

Another group of amines suitable for use as amine reactant (III) are branched polyalkylene polyamines. The branched polyalkylene polyamines are polyalkylene polyamines wherein the branched- group is a side chain containing on the average at least one nitrogen-bonded aminoalkyl group.

These reactants may be expressed by the formula:

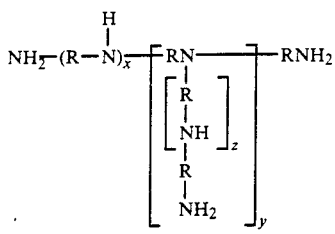 (V)

wherein R is an alkylene group such as ethylene, propylene, butylene and other homologues (both straight chained and branched), etc., but preferably ethylene; and x, y and z are integers, x being for example, from 4 to 24 or more but preferably 6 to 18, y being for example 1 to 6 or more but preferably 1 to 3, and z being for example 0 to 6 but preferably 0 to 1. The x and y units may be sequential, alternative, orderly or randomly distributed.

A preferred class of such polyamine reactants includes those of the formula

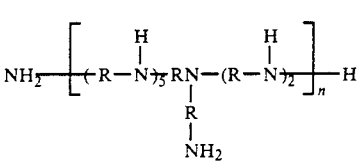 (VI)

wherein n is an integer, for example, 1-20 or more but preferably 1-3, wherein R is preferably ethylene, but may be propylene, butylene, etc. (straight chained or branched).

U.S. Pat. Nos. 3,200,106 and 3,259,578 are expressly incorporated herein by reference for their disclosure of how to make such polyamines.

Suitable amines also include polyoxyalkylene polyamines, e.g., polyoxyalkylene diamines and polyoxyalkylene triamines, having average molecular weights ranging from about 200 to 4000 and preferably from about 400 to 2000. Illustrative examples of these polyoxyalkylene polyamines may be characterized by the formula:

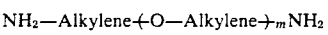 (VIIA)

wherein m has a value of about 3 to 70 and preferably about 10 to 35.

 (VIIB)

wherein n is such that the total value is from about 1 to 40 with the proviso that the sum of all of the n's is from about 3 to about 70 and generally from about 6 to about 35 and R is a polyvalent saturated hydrocarbon radical of up to 10 carbon atoms having a valence of 3 to 6. The alkylene groups may be straight or branched chains and contain from 1 to 7 carbon atoms, and usually from 1 to 4 carbon atoms. The various alkylene groups present within Formulae VII and VIII may be the same or different.

The preferred polyoxyalkylene polyamine reactants useful for the purposes of this invention include the polyoxyethylene and polyoxypropylene diamines and the polyoxypropylene triamines having average molecular weights ranging from about 200 to 2000. The polyoxyalkylene polyamines are commercially available and may be obtained, for example, from the Jefferson Chemical Company, Inc. under the trade name "Jeffamines D-230, D-400, D-1000, D-2000, T-403, etc.".

U.S. Pat. Nos. 3,804,763 and 3,948,800 are expressly incorporated herein by reference for their disclosure of such polyoxyalkylene polyamine reactants.

Another preferred class of amine reactants for use in the present invention is alkylene polyamines, including the polyalkylene polyamines, which are described in more detail hereafter. The alkylene polyamines include those conforming to the formula

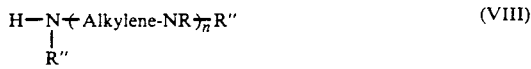 (VIII)

wherein n is from 1 to about 10; each R″ is independently a hydrogen atom, a hydrocarbyl group or a hydroxy-substituted hydrocarbyl group having up to about 30 atoms, and the "Alkylene" group has from 1 to about 10 carbon atoms, but the preferred alkylene is ethylene or propylene. Especially preferred are the alkylene polyamines where each R″ is hydrogen with the ethylene polyamines and mixtures of ethylene polyamines being the most preferred. Usually n will have an average value of from about 2 to about 7. Such alkylene polyamines include methylene polyamine, ethylene polyamines, butylene polyamines, propylene polyamines, pentylene polyamines, hexylene polyamines, heptylene polyamines, etc. The higher homologs of such amines and related aminoalkylsubstituted piperazines are also included.

Alkylene polyamines useful in preparing the carboxylic derivative compositions include ethylene diamine, triethylene tetramine, propylene diamine, trimethylene diamine, hexamethylene diamine, decamethylene diamine, octamethylene diamine, di(heptamethylene)triamine, tripropylene tetramine, tetraethylene pentamine, trimethylene diamine, pentaethylene hexamine, di(trimethylene)triamine, N-(2-aminoethyl)piperazine, 1,4-bis(2-aminoethyl)piperazine, and the like. Higher homologs, as are obtained by condensing two or more of the above-illustrated alkylene amines, are useful as reactant (III) as are mixtures of two or more of any of the aforedescribed polyamines.

Ethylene polyamines, such, as those mentioned above, are especially useful for reasons of cost and effectiveness. Such polyamines are described in detail under the heading "Diamines and Higher Amines" in The Encyclopedia of Chemical Technology, Second Edition, Kirk and Othmer, Volume 7, pages 27–39, Interscience Publishers, Division of John Wiley and Sons, 1965, which is hereby incorporated by reference for their disclosure of useful polyamines. Such compounds are prepared most conveniently by the reaction of an alkylene chloride with ammonia or by reaction of an ethylene imine with a ring-opening reagent such as ammonia, etc. These reactions result in the production of the somewhat complex mixtures of alkylene polyamines, including cyclic condensation products such as piperazines.

Other useful types of polyamine reactant mixtures are those resulting from stripping of the above-described polyamine mixtures. In this instance, lower molecular weight polyamines and volatile contaminates are removed from an alkylene polyamine mixture to leave as residue what is often termed "polyamine bottoms". In general, alkylene polyamine bottoms can be characterized as having less than two, usually less than 1% by weight material boiling below about 200° C. In the instance of ethylene polyamine bottoms, which are readily available and found to be quite useful, the bottoms contain less than about 2% by weight total diethylene triamine (DETA) or triethylene tetramine (TETA). A typical sample of such ethylene polyamine bottoms obtained from the Dow Chemical Company of Freeport, Texas designated "E-100" showed a specific gravity at 15.6° C. of 1.0168, a percent nitrogen by weight of 33.15 and a viscosity at 40° C. of 121 centistokes. Gas chromatography analysis of such a sample showed it to contain about 0.93% "Light Ends" (DETA), 0.72% TETA, 21.74% tetraethylene pentamine and 76.61% pentaethylene hexamine and higher (by weight). These alkylene polyamine bottoms include cyclic condensation products such as piperazine and higher analogs of diethylene triamine, triethylene tetramine and the like.

A preferred group of polyamine reactants useful for the present invention includes polyamines of formula (II):

 (II)

in which each R is hydrogen or a hydrocarbyl group; each R′ is independently hydrogen, alkyl, or NH₂R″(NR″)_y—wherein each R″ is independently an alkylene group of 1 to about 10 carbon atoms and y is a number in the range of from 1 to about 6; each Z is independently an alkylene group of 1 to about 10 carbon atoms, a heterocyclic nitrogen containing cycloalkylene or an oxyalkylene group of 1 to about 10 carbon atoms and x is a number in the range of from 1 to about 10.

The hydroxy alkyl and hydroxy aryl reactants as represented by Formula (II) hereinabove are preferably polyhydroxy materials which will condense with the above discussed amine reactants and more preferably will condense to very high molecular weight materials as opposed to forming cyclic products. The hydroxy containing reactant may be selected from aliphatic, cycloaliphatic, and aryl based radicals wherein the radical is preferably an alkyl based radical and most preferably a hydroxyethyl radical. These hydroxy containing materials may contain other functional groups so long as they do not interfere with the condensation with the amine reactant or adversely affect the properties of the resultant high molecular weight polyamine condensate.

Aside from the above-discussed limitations on the hydroxy containing reactant, this reactant may be selected from numerous hydroxy containing compounds or species inclusive, but not exclusive thereof, of such hydroxy containing materials there may be mentioned, polyalkylene polyols, alkylene glycols and polyoxyalkylene polyols such as polyoxyethylene polyols, polyoxypropylene polyols, polyoxybutylene polyols, and the like. These polyoxyalkylene polyols (sometimes called polyglycols) can contain up to about 150 oxyalkylene groups wherein the alkylene radical contains from 2 to about 8 carbon atoms. Such polyoxyalkylene polyols are generally dihydric alcohols. That is, each end of the molecule terminates with an -OH group. In order for such polyoxyalkylene alcohols to be useful as a reactant, there must be at least two such -OH groups. The monoethers of these alkylene glycols and polyoxyalkylene glycols are also useful as reactants. These include the monoaryl ethers, monoalkyl ethers, and monoaralkyl ethers of these alkylene glycols and polyoxyalkylene glycols. This group of alcohols may be represented by the general formula HO R$_A$O$_p$R$_B$OR$_C$ (IX)

wherein RC is aryl such as phenyl, lower alkoxy phenyl, or lower alkyl phenyl; lower alkyl such as ethyl, propyl, tert-butyl, pentyl, etc.,; and aralkyl such as benzyl, phenylethyl, phenylpropyl, p-ethylphenylethyl, etc.; p is zero to about 150, and R$_A$ and R$_B$ are lower alkylene of 2 to about 8 carbon atoms and, preferably, 2 to 4 carbon atoms. Polyoxyalkylene glycols where the alkylene groups are ethylene or propylene and p is at least two as well as the monoethers thereof as described above are considered very useful for the purposes of the present invention.

The aryl polyhydric alcohols useful as the hydroxy reactant include polyhydric phenols and naphthols, which are the preferred hydroxyaromatic compounds. These hydroxy-substituted aromatic compounds may contain other substituents in addition to the hydroxy substituents such as halo, alkyl, alkenyl, alkoxy, alkylmercapto, nitro and the like. Usually, the hydroxy aromatic compound will contain 1 to 4 hydroxy groups. The aromatic hydroxy compounds are illustrated by the following specific examples: beta-naphthol, p-nitrophenol, alpha-naphthol, cresols, resorcinol, catechol, thymol, eugenol, p,p'-di-hydroxy-biphenyl, hydroquinone, pyrogallol, phloroglucinol, hexyl-resorcinol, orcinol, guaiacol, alpha-decyl-beta-naphthol, the condensation product of heptyl phenol with 0.5 moles of formaldehyde, the condensation product of octylphenol with acetone, di(hydroxyphenyl) oxide, di(hydroxyphenyl)sulfide, di-(hydroxyphenyl) disulifde.

Other specific alcohols useful as the hydroxy containing reactant are the ether alcohols and amino alcohols including, for example, the oxyalkylene, oxy-arylene-, amino-alkylene-, and amino-arylene-substituted alcohols having one or more oxyalkylene, aminoalkylene or amino-aryleneoxy-arylene radicals. They are exemplified by Cellosolve, carbitol, mono-(heptylphenyloxypropylene)-substituted glycerol, poly(styreneoxide), aminoethanol, di(hydroxyethyl)amine, tri(hydroxypropyl)amine, N,N,N',-N'-tetrahydroxytrimethylenediamine, and the like.

The polyhydric alcohol reactants of the present invention preferably contain from 2 to about 10 hydroxy radicals. They are illustrated, for example, by the alkylene glycols and polyoxyalkylene glycols mentioned above such as ethylene glycol, diethylene glycol, triethylene glycol, tetraethylene glycol, dipropylene glycol, tripropylene glycol, dibutylene glycol, tributylene glycol, and other alkylene glycols and polyoxyalkylene glycols in which the alkylene radicals contain 2 to about 8 carbon atoms.

A preferred class of alcohols suitable as reactant (II) are those polyhydric alcohols containing up to about 12 carbon atoms, and especially those containing 3 to 10 carbon atoms. This class of alcohols includes glycerol, erythritol, pentaerythritol, dipentaerythritol, gluconic acid, glyceraldehyde, glucose, arabinose, 1,7-heptanediol, 2,4-heptanediol, 1,2,3-hexanetriol, 1,2,4-hexanetriol, 1,2,5-hexanetriol, 2,3,4-hexanetriol, 1,2,3-butanetriol, 1,2,4-butanetriol, 2,2,6,6-tetrakis-(hydroxymethyl)cyclo-hexanol, 1,10-decanediol, digitalose, and the like. Aliphatic alcohols containing at least three hydroxyl groups and up to five hydroxyl groups are particularly preferred.

Amino alcohols contemplated as suitable for use as the hydroxy containing reactant have two or more hydroxy groups. Examples of suitable amino alcohols are the N-(hydroxy-lower alkyl)amines and polyamines such as di-(2-hydroxyethyl)-amine, tri-(2-hydroxyethyl)-amine, N,N,N'-tri-(2-hydroxyethyl)ethylenediamine, N-(2-hydroxy-propyl)-5-carbethoxy-2-piperidone, and ethers thereof with aliphatic alcohols, especially lower alkanols, N,N-di-(3-hydroxypropyl)glycine, and the like. Also contemplated are other poly-N-hydroxyalkyl-substituted alkylene polyamines wherein the alkylene polyamine are as described above; especially those that contain 2 to 3 carbon atoms in the alkylene radicals.

Polyoxyalkylene polyols which have two or three hydroxyl groups and molecules consisting essentially of hydrophobic portions comprising $$-\underset{R_D}{\overset{|}{C}}HCH_2O-$$

groups wherein R$_D$ is lower alkyl of up to three carbon atoms and hydrophilic portions comprising —CH$_2$CH$_2$O—groups are a preferred hydroxy continuing reactant. Such polyols can be prepared by first reacting a compound of the formula R$_E$(OH)$_q$ where q is 2–3 and R$_E$ is hydrocarbyl with a terminal alkylene oxide of the formula $$R_D-CH\underset{O}{\overset{}{\diagdown\diagup}}CH_2$$

and then reacting that product with ethylene oxide. R$_E$(OH)$_q$ can also be, for example, (trimethylolpropane), (trimethylolethane), ethylene glycol, trimethylene glycol, tetramethylene glycol, tri-(beta-hydroxypropyl)amine, 1,4-(2-hydroxyethyl)-cyclohexane, (tris-(hydroxymethyl)amino methane, 2-amino-2-methyl-1,3-propane diol, N,N,N',N'-tetrakis(2-hydroxypropyl)ethylene diamine, N,N,N',N'-tetrakis(2-hydroxyethyl)-ethylene diamine, resorcinol, or one of the other illustrative examples mentioned hereinbefore. The foregoing described R$_E$(OH)$_q$ polyols may also be used alone as the hydroxy containing (II) reactant.

Other hydroxy containing reactants useful in the present invention are hydroxyalkyl, hydroxy alkyl oxyalkyl and hydroxy aryl sulfides of the formula S$_f$(R$_F$OH)$_{2f}$ (X)

wherein f is 1 or 2 and R$_F$ is alkyl of 1 to about 10 carbon atoms alkyl oxyalkyl where alkyl is 1 to about 10 carbon atoms and preferably 2 to 4 carbon atoms, and aryl of at least 6 carbon atoms. For the purposes of the present invention, 2,2'-thiodiethanol and 2,2'-thiodipropanol are the preferred, reactants for this class of hydroxy containing reactants.

Preferred combinations of reactants for making the polyamines of the present invention include those in which reactant (A) is a polyhydric alcohol of formula (II) having three hydroxy groups or an amino alcohol of formula (II) having two or more hydroxy groups and reactant (B) is an alkylene polyamine having at least two primary nitrogen atoms and wherein the alkylene group contains 2 to about 10 carbon atoms; and wherein the reaction is conducted in the presence of an acid catalyst at an elevated temperature.

As indicated previously, the reaction of the amine reactant with the hydroxy alkyl or hydroxy aryl reactant requires the presence of an acid catalyst. Those catalysts useful for the purpose of this invention include mineral acids (mono, di- and poly basic acids) such as sulfuric acid and phosphoric acid; organo phosphorus acids and organo sulfonic acids such as $R^*P(O)(OH)_2$ and $R^*SO_3H$, wherein $R^*$ is hydrocarbyl; alkali metal partial salts of $H_3PO_4$ and $H_2SO_4$, such as $NaHSO_4$, $LiHSO_4$, $KHSO_4$, $NaH_2PO_4$, $LiH_2PO_4$ and $KH_2PO_4$; alkaline earth metal partial salts of $H_3PO_4$ and $H_2SO_4$, such as $CaHPO_4$, $CaSO_4$ and $MgHPO_4$; also $Al_2O_3$ and Zeolites. Phosphoric acid is preferred because of its commercial availability and ease of handling. Also useful as catalysts for this invention are materials which generate acids when treated in the reaction mixture, e.g., triphenylphosphite.

The reaction is run at an elevated temperature which, depending upon the particular reactants, can range from 60° C. to about 265° C. Most reactions, however, are run in the 220° C. to about 250° C. range. Furthermore, this reaction may be run at atmospheric pressure or optionally at a reduced pressure depending upon the particular reactants and the concomitant economics. The degree of condensation of the resultant high molecular weight polyamine prepared by the process of the present invention is limited only to the extent to prevent the formation of solid products under reaction conditions. The control of the degree of condensation of the product of the present invention is normally accomplished by limiting the amount of the condensing agent, i.e., the hydroxy alkyl or hydroxy ayrl reactant charged to the reaction medium. In a preferred embodiment, the condensed high molecular weight polyamines of the present invention are pourable at room temperature and have viscosities which range from about 100% greater than the viscosity of the amine reactant (III) to about 6000% greater than the viscosity of the amine reactant (III).

In another preferred embodiment, the condensed high molecular weight polyamines of the present invention have viscosities which range from 50% to about 1000% greater than the viscosity of the amine reactant (III). In a most preferred embodiment, the viscosity of these polyamines will range from about 50 cSt to about 200 cSt at 100° C. It is pointed out that the foregoing limitation on the degree of condensation of the products of the present invention is solely for the purpose of the ultimate end use of these materials in lubricant compositions. For other or related utilities, solid products of the condensation reaction described above may be desirable and thus the condensation may be carried out to result in high molecular weight solid products where this may be accomplished by adjusting the relative amounts of the respective reactants charged to the reaction medium.

The preparation of various high molecular weight polyamine condensates representative of products within the scope of the present invention is illustrated in the following examples. While these examples will show one skilled in the art how to operate within the scope of this invention, they are not to serve as a limitation on the scope of the invention where such scope is defined only in the claims. It is pointed out that in the following examples, and elsewhere in the present specification and claims, all percentages and all parts are intended to express percent by weight and parts by weight unless otherwise clearly indicated.

EXAMPLE I

A 4-necked, 500-ml, round-bottom flask equipped with glass stirrer, thermowell, subsurface $N_2$ inlet, Dean-Stark trap, and Friedrich condenser was charged with a) 201 grams of Tetraethylenepentamine (TEPA).
b) 151 grams of 40% aqueous Tris(hydroxymethyl)-aminomethane (THAM), and
c) 3.5 grams of 85% $H_3PO_4$.

The mixture was heated to 120° C. over 1.0 hour. With $N_2$ sweeping, the mixture was heated to 130° C. over 1 hour and to 230° C. over 2 hours more. Held at 230°–240° C. for 4 hours and at 241°–250° C. for 3 hours. The product was cooled to 150° C. and filtered with diatomaceous earth filter aid.

EXAMPLE II

A 4-necked, 3-1, round-bottom flask was equipped with glass stirrer, thermowell, subsurface $N_2$ inlet, Dean-Stark trap, and Friedrich condenser was charged with:

a) 1299 grams of HPA Taft Amines (amine bottoms).
b) 727 grams of 40% aqueous Tris(hydroxymethyl)-aminomethane (THAM).

The mixture was heated to 60° C. and 23 grams of 85% $H_3PO_4$ was added. The mixture was heated to 120° C. over 0.6 hr. With $N_2$ sweeping, the mixture was heated to 150° C. over 1.25 hr. and to 235° C. over 1 hr. more. Held at 230°–235° C. for 5 hr. Heated to 240° C. over 0.75 hr. and held at 240°–245° C. for 5 hr. The product was cooled to 150° C. and filtered with a diatomaceous earth filter aid. Yield: 84% (1221 grams).

EXAMPLE III

A 3-liter flask equipped with stirrer, thermowell, below surface $N_2$ inlet and a stripping condenser was charged with 363 grams of THAM and 1200 grams of TEPA. Next was added 16 grams of $H_3PO_4$ at 110° C. $N_2$ blowing was commenced at 0.25 cfh. The mixture was then heated to 220° C. in 0.8 hour and held at 220°–225° C. for 1.2 hour; then heated to 230° C. in 0.2 hour and held at 230° C. for 4.75 hours: 129g distillate collected. The mixture stood and was held at 242°–245° C. for 5 hours: 39g of additional distillate was collected in trap. Held at 246°–255° C. for 1.2 hr: 178g material in trap; NNBbpb=170. The mixture was filtered at 155° C. using 45g of a diatomaceous earth filter aid.

EXAMPLE IV

A 3-liter flask equipped with stirrer, thermowell, below surface $N_2$ inlet and a stripping condenser was charged with 363 grams of THAM and 1200 grams of TEPA. 16 grams of $H_3PO_4$ was added at 100° C. $N_2$ blowing was commenced at 0.2 cfh. The mixture was heated to 165° C. in 0.4 hour; and to 241° C. in 0.6 hour. Held at 241°–243° C. for 0.3 hour. The contents were further heated to 250° C. for an additional 0.5 hour and held at 250° C. for 5.5 hour: 288g of material was collected in the trap; NNBbpb=506. This material was filtered at 150° C. using 55g of diatomaceous earth filter aid.

EXAMPLE V

A 1-liter flask equipped with stirrer, thermowell, below surface $N_2$ inlet and Dean-Stark trap was charged with 121 grams of THAM and 400 grams of TEPA. To this mixture was added 8.2 grams of $KH_2PO_4$ at 60° C. $N_2$ blowing was commenced at a 0.15 cfh. The reaction mixture was heated to 150° C. over 1 hour to 230° C. and over another 1.5 hours. The temperature was held at 230° C.-232° C. for 4.25 hour: 17g material collected in trap. The heated mixture was allowed to stand and was held at 237° C. for 3.25 hour: 38g material collected in trap. The mixture was further heated to 241° C. over 0.75 hour and held at 241° C.-242° C. for 4.75 hr.: 50g of material collected in trap. The material was allowed to stand and then held at 250° C. for 5 hour: total of 53g material collected in trap: NNBbph=96.5. Filtered at 150° C. using 20g of diatomaceous earth filter aid.

EXAMPLE VI

To a 500ml flask equipped with stirrer, thermowell, below surface $N_2$ inlet to Dean-Stark trap was charged with 201 grams of TEPA and 468 grams of gylcerol. 2.3 grams $H_3PO_4$ were added at 80° C. $N_2$ blowing was commenced at 0.35 cfh. The mixture was heated to 220° C. over 2 hours; to 240° C. in 1 hour; to 245° C. in 1.5 hour and to 255° C. in 1 hour. The temperature was held at 255°-252° C. for 2 hours: 12g material collected in trap. The mixture was allowed to stand and held at 255°-262° C. for 7 hours: 34g material collected in trap. The temperature of the mixture was further held at 255°-260° C. for 1 hour more. A total of 36g collected in trap: NNBbph=435. Filtered at 130° C. using 23g of diatomaceous earth filter aid.

EXAMPLE VII

To a 500ml flask equipped with stirrer, thermowell, below surface $N_2$ inlet and Dean-Stark trap was charged 201 grams of TEPA and 45 grams of hexaglycerol. To this mixture 3.5 grams of $H_3PO_4$ was added at 85° C. $N_2$ blowing was commenced at 0.35 cfh. The mixture was heated to 245° C. over 0.7 hour and held at 245° C.-260° C. for 1.75 hour: 10g of material collected in trap. The mixture was allowed to stand and held at 260° C.-270° C. for 7.5 hour: total of 27g of material collected in trap: NNBbph=645 Filtered at 125° C. using 20g of diatomaceous earth filter aid.

HIGHLY CONDENSED POLYAMINES FURTHER REACTED TO FORM DISPERSANT MATERIALS

While the high molecular weight condensed polyamines of the present invention are useful by themselves as lubricant and fuel additives and dispersants, they may be further reacted to form even higher molecular weight lubricant and fuel dispersant materials. In general, materials which may be used to further react with polyamine materials of the present invention are materials known to those skilled in the art and are described in numerous books, articles and patents. A number of these reference materials are noted hereinbelow in relation to specific types of dispersants and, where this is done, it is to be understood that they are incorporated by reference for their disclosures relevant to the subject matter discussed at the point in the specification in which they are identified.

CARBOXYLIC ACID OR PHENOL REACTANT MATERIALS

Among the reactant materials that may be used for the purposes of the present invention to react with the above-described polyamines to form the higher molecular weight dispersant materials, there may be first mentioned carboxylic acids. The carboxylic acids from which suitable neutral and basic salts for use in this invention can be made include aliphatic, cycloaliphatic, and -aromatic mono- and polybasic carboxylic acids such as the naphthenic acids, alkyl- or alkenyl-substituted cyclopentanoic acids, alkyl- or alkenyl-substituted cyclohexanoic acids, alkyl- or alkenyl-substituted aromatic carboxylic acids. The aliphatic acids generally contain at least eight carbon atoms and preferably at least twelve carbon atoms. Usually, they have no more than about 400 carbon atoms. Generally, if the aliphatic carbon chain is branched, the acids are more oil-soluble for any given carbon atoms content. The cycloaliphatic and aliphatic carboxylic acids can be saturated or unsaturated. Specific examples include 2-ethylhexanoic acid, -linolenic acid, propylene-tetramer-substituted maleic acid, behenic acid, isostearic acid, pelargonic acid, capric acid, palmitoleic acid, linoleic acid, lauric acid, oleic acid, ricinoleic acid, undecyclic acid, dioctylcyclopentane carboxylic acid, myristic acid, dilauryldecahydronaphthalene carboxylic acid, stearyl-octahydroindene carboxylic acid, palmitic acid, commercially available mixtures of two or more carboxylic acids such as tall oil acids, rosein acids and the like.

A preferred group of oil-soluble carboxylic acids useful in preparing the salts used in the present invention are the oil-soluble aromatic carboxylic acids. These acids are represented by the general formulae:

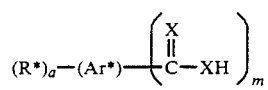

Formula XIII where R* is an aliphatic hydrocarbon-based group of at least four carbon atoms, and no more than about 400 aliphatic carbon atoms, a is an integer of from one to four, Ar* is a polyvalent aromatic hydrocarbon nucleus of up to about 14 carbon atoms each X is independently a sulfur or oxygen atom, and m is an integer of from one to four with the proviso that R* and a are such that there is an average of at least 8 aliphatic carbon atoms provided by the R* groups for each acid molecule represented by Formula XIII. Examples of aromatic nuclei represented by the variable Ar* are the polyvalent aromatic radicals derived from benzene, naphthalene, anthracene, phenanthrene, indene, fluorene, biphenyl, and the like. Generally, the radical represented by Ar* will be polyvalent nucleus derived from benzene or naphthalene such as phenylenes and naphthylene, e.g., methylphenylenes, ethoxyphenylenes, nitrophenylenes, isopropylphenylenes, hydroxyphenylenes, mercaptophenylenes, N,N-diethylaminophenylenes, chlorophenylenes, dipropoxynaphthylenes, triethylnaphthylenes, and similar tri-, tetra-, pentavalent nuclei thereof, etc.

The R* groups are usually purely hydrocarbyl groups, preferably groups such as alkyl or alkenyl radicals. However, the R* groups can contain small number substituents such as phenyl, cycloalkyl (e.g., cyclohexyl, cyclopentyl, etc.) and nonhydrocarbon groups such as nitro, amino, halo (e.g., chloro, bromo, etc.), lower alkoxy, lower alkyl mercapto, oxo substituents (i.e.,=O), thio groups (i.e.,=S), interrupting groups such as —NH—, —O—, —S—and the like provided the essentially hydrocarbon character of the R* group is retained. The hydrocarbon character is retained for purposes of this invention so long as any non-carbon atoms present in the R* groups do not account for more than about 10% of the total weight of the R* groups.

Examples of R* groups include butyl, isobutyl, pentyl, octyl, nonyl, dodecyl, docosyl, tetracontyl, 5-chlorohexyl, 4-ethyoxypentyl, 4-hexenyl, 3-cyclohexyloctyl, 4-(p-chloro-phenyl)-octyl, 2,3,5-trimethylheptyl, 4-ethyl-5-methyloctyl, and substituents derived from polymerized olefins such as polychloroprenes, polyethylenes, polypropylenes, polyisobutylenes, ethylene-propylene copolymers, chlorinated olefin polymers, oxidized ethylene-propylene copolymers and the like. Likewise, the group Ar* may contain non-hydrocarbon substituents, for example, such diverse substituents as lower alkoxy, lower alkyl mercapto, nitro, halo, alkyl or alkenyl groups of less than four carbon atoms, hydroxy, mercapto and the like.

A group of particularly useful carboxylic acids are those of the formulae:

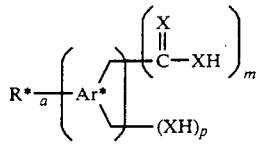

Formula XIV where R*, X, Ar*, m and a are as defined in Formula XIII and p is an integer of 1 to 4, usually 1 or 2. Within this group, an especially preferred class of oil-soluble carboxylic acids are those of the formulae:

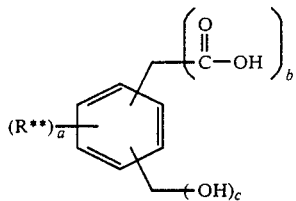

Formula XV where R in Formula X is an aliphatic hydrocarbon group containing at least 4 to about 400 carbon atoms, a is an integer of from 1 to 3, b is 1 or 2, c is zero, 1, or 2 and preferably 1 with the proviso that R and a are such that the acid molecules contain at least an average of about twelve aliphatic carbon atoms in the aliphatic hydrocarbon substituents per acid molecule. And within this latter group of oil-soluble carboxylic acids, the aliphatic-hydrocarbon substituted salicylic acids wherein each aliphatic hydrocarbon substituent contains an average of at least about sixteen carbon atoms per substituent and one to three substituents per molecule are particularly useful. Salts prepared from such salicylic acids wherein the aliphatic hydrocarbon substituents are derived from polymerized olefins, particularly polymerized lower 1-mono-olefins such as polyethylene, polypropylene, polyisobutylene, ethylene-/propylene copolymers and the like and having average carbon contents of about 30 to about 400 carbon atoms.

The carboxylic acids corresponding to Formula XIII-XV, above are well known or can be prepared according to procedures known in the art. Carboxylic acids of the type illustrated by the above formula and processes for preparing their neutral and basic metal salts are well known and disclosed, for example, in such U.S. Pat. Nos. as 2,197,832; 2,197,835; 2,252,662; 2,252,664; 2,174,092; 3,410,798 and 3,595,791.

Another type of neutral and basic carboxylate salt used in this invention are those from alkenyl succinates of the general formula:

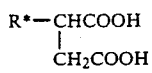

Formula XVI wherein R* is as defined above in Formula X. Such salts and means for making them are set forth in U.S. Pat. Nos. 3,271,130; 3,567,637 and 3,632,510, which are hereby incorporated by reference in this regard.

An example of a desirable R* group is a polyalkylene group characterized by an Mn value of 150 to about 5000 and Mw/Mn value of about 1.5 to about 4.0.

Other patents specifically describing techniques for making basic salts of the hereinabove-described sulfonic acids, carboxylic acids, and mixtures of any two or more of these include U.S. Pat. Nos. 2,501,731; 2,616,904; 2,616,905; 2,616,906; 2,616,911; 2,616,924; 2,616,925; 2,617,049; 2,777,874; 3,027,325; 3,256,186; 3,282,835; 3,384,585; 3,373,108; 3,365,396; 3,342,733; 3,320,162; 3,312,618; 3,318,809; 3,471,403; 3,488,284; 3,595,790 and 3,629,109. The disclosures of these patents are hereby incorporated in this present specification for their disclosures in this regard as well as for their disclosure of specific suitable basic metal salts.

Neutral and basic salts of phenols (generally known as phenates) are also useful in the compositions of this invention and well known to those skilled in the art. The phenols from which these phenates are formed are of the general formula:

 Formula XVII wherein R*, a, Ar*, X and m have the same meaning and preferences as described hereinabove with reference to Formula XIII. The same examples described with respect to Formula XI also apply.

A commonly available class of phenates are those made from phenols of the general formula:

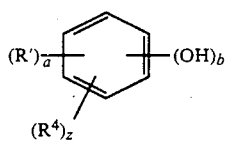

Formula XVIII wherein a is an integer of 1-3, b is of 1 or 2, z is 0 or 1, R' in Formula XIII is a substantially saturated hydrocarbon-based substituent having an average of from 30 to about 400 aliphatic carbon atoms and $R^4$ is selected from the group consisting of lower alkyl, lower alkoxyl, nitro and halo groups.

One particular class of phenates for use in this invention are the basic (i.e., overbased, etc.) Group IIA metal sulfurized phenates made by sulfurizing a phenol as described hereinabove with a sulfurizing agent such as sulfur, a sulfur halide, or sulfide or hydrosulfide salt.

Techniques for making these sulfurized phenates are described in U.S. Pat. Nos. 2,680,096; 3,036,971 and 3,775,321 which are hereby incorporated by reference for their disclosures in this regard.

Other phenates that are useful are those that are made from phenols that have been linked through alkylene (e.g., methylene) bridges. These are made by reacting single or multi-ring phenols with aldehydes or ketones, typically, in the presence of an acid or basic catalyst. Such linked phenates as well as sulfurized phenates are described in detail in U.S. Pat. No. 3,350,038; particularly columns 6–8 thereof, which is hereby incorporated by reference for its disclosures in this regard.

Naturally, mixtures of two or more neutral and basic salts of the hereinabove described carboxylic acids and phenols can be used in the compositions of this invention, including mixtures of two or more of any of these The above-described reaction products form additive/dispersant materials of the general formula:

[(QT$_t$)$_v$J$_j$]   Formula XIX wherein Q represents the non-reactive portion of the hereinabove described carboxylic acid or phenol reactant material; T represents the reactive moiety of the particular carboxylic acid and/or phenol reactant which is acyl, acyloxy, oxyalkylene, arylene or imidoyl; J represents the condensed portion of the hereinabove described high molecular weight polyamines; the same as defined herein; and t and j are independently a whole integer of a least.

The foregoing dispersants are generally prepared in the same manner as the high molecular weight polyamines of the present invention. In other words, they are prepared by the acid catalyzed condensation reaction of at least one of the high molecular weight polyamines of the present invention with at least one of the reactive materials described hereinabove at an elevated temperature. The catalysts previously described herein are also useful in this reaction.

These dispersants generally have a total base number of about 45 to about 90, and more particularly in the range of about 55 to about 80.

In one embodiment, a high molecular weight additive/dispersant for lubricant and fuel compositions may be prepared by reacting (A) hydrocarbyl substituted carboxylic acids or derivatives thereof containing at least about 34 carbon atoms with (B) at least one polyamine reactant derived from a hydroxyalkyl or hydroxyaryl compound of the formula:

(R$_n$Y X$_q$AOH)$_m$   (I)

wherein each R is independently hydrogen or a hydrocarbyl, Y represents S, N, or O; A and X each independently represent an alkylene group; n is 0, 1 or 2 dependent upon m and q, where q is 0 or 1 and m is 1, 2, or 3 and

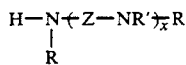   (II)

wherein
each R is hydrogen or a hydrocarbyl group,
each R' is independently hydrogen, alkyl, or NH$_2$R"(NR")$_y$- wherein each R" is independently an alkylene group of 1 to about 10 carbon atoms and y is a number in the range of from 1 to about 6,
each Z is independently an alkylene group of 1 to about 10 carbon atoms, a heterocyclic nitrogen containing cycloalkylene or oxyalkylene of 1 to about 10 carbon atoms and
x is a number in the range of from 1 to about 10.

The additive dispersants made according to the aforementioned process exhibit a total base number in the range from about 3 to about 90 and, in one embodiment, may have a total base number in the range from about 55 to about 85.

One embodiment of the additive dispersants made according to the aforementioned process having a base number in the range from 3 to about 90 is at least one substituted succinic acid or derivative thereof consisting of substituent groups and succinic groups wherein the substituent groups are derived from polyalkylene, said polyalkylene being characterized by a Mn value of 1,300 to about 5,000 and a Mw/Mn value of 1.5 to about 4.0, and wherein said polyamine is derived from a hydroxyalkyl or hydroxyaryl compound selected from the group consisting of glycerol, trimethylolpropane, trimethylolethane and tris(hydroxymethyl)aminomethane and an amine compound selected from the group consisting of triethylenetetramine, diethylenetriamine, tetraethylenepentamine, pentaethylene-hexamine and mixtures thereof.

Specifically, Q may be derived from a polyalkylene-substituted succinic acid or derivative thereof wherein said polyalkylene substituent is characterized by a Mn value of 150 to about 5000 and a Mw/Mn value of about 1.5 to about 4.0.

The following examples are provided to illustrate various dispersants prepared or derived from reaction of the polyamine materials of the present invention with such dispersant materials as described above. Again, it is emphasized that these examples are provided for illustrative purposes only and are not to serve as a limitation on the scope of the invention where such scope is set out solely in the claims.

EXAMPLE A

A 12-1, 4-necked, round-bottom flask equipped with stirrer, thermowell, subsurface N$_2$ inlet, Dean-Stark trap and Friedrich condenser was charged with (a) 460 g. TEPA/THAM(5N:1.50H) polyamine, H$_3$PO$_4$ cat and (b) 2500 g. 2C Dil oil. The mixture was heated to 105° C. and 3360 g. of a poly(isobutene)(molecular weight 1000)-substituted succinic anhydride having a saponification number of 100 was added through a funnel over 1.5 hour. N$_2$ blowing was commenced slowly. The mixture was heated to 160° C. and held for 5.0 hours. The mixture was filtered at 150° C. with diatomaceous earth filter aid to give the final product. Yield: 96% (5991 g), 40% 2C Dil oil. Analysis: %N=2.31'/3=2.42; Free Amine =Nil; TBN(776)=49.1.

EXAMPLE B

A 12-1, 4-necked, round-bottom flask equipped with stirrer, thermowell, subsurface N$_2$ inlet, Dean-Stark trap and Friedrich condenser was charged with (a) 605 grams HPA Taft Amines/THAM(5N:1.20H) polyamine, H$_3$PO$_4$Cat and (b) 3262 grams 2c dil oil. The mixture was heated to 110° C. and 4300 grams of a poly(isobutene)(molecular weight 1000)- substituted succinic anhydride having a saponification number of 100 was added through a funnel over 0.7 hour. N₂ blowing was commenced slowly. The mixture was heated to 160° C. over 1 hour and held at 160°-162° C. for 5 hours.

The mixture was filtered at 150° C. with diatomaceous earth filter aid to give the final product. Yield: 96% (8155g), 40% 2c dil oil. Analysis: %N =2.28/2.19; TBN(776)=46.5; TAN(744)=7.7.

EXAMPLE C

A 1-liter flask equipped with stirrer, thermowell and reflux condenser was charged with 39g of the reaction product of Example IV and 75g MeOH. This mixture was heated and stirred clear solution at 40° C. To the mixture 2c dil oil was added at 40° C. A solution of 218g of of a poly(isobutene)(molecular weight 1000)- substituted succinic anhydride having a saponification number of 100 in 110g MePh was added over 0.8 hour at 62°-50° C. This mixture was held at 50°-65° C. for 1 hour. This mixture was stripped to 110° C. in 1.5 hour; to 120° C. in 1 hour; to 160° C. in 0.8 hour more. N₂ blowing was commenced slowly at 0.15 cfh and held at 160° C. for 6.0 hours and then filtered at 150° C. using 25g of diatomaceous earth filter aid.

EXAMPLE D

To a 1-liter flask equipped with stirrer, thermowell, below surface N₂ inlet and Dean-Stark trap was charged 64.6g of the product of Example I and 168 grams of a diluent oil. To this mixture was added 110g of a poly(propylene) (molecular weight 168)- substituted succinic anhydride having a saponification number of 420 over 0.1 hour at 110° C.-135° C. (exc). N₂ blowing was commenced slowly at 0.15 cfh. The mixture was held at 130° C.-130° C. for 0.2 hour. The mixture was heated to 165° C over 0.8 hour and held at 165° C. for 4.5 hour. The mixture was allowed to stand. 56g on Vcon LB625 was added. The mixture was filtered at 145° C. using 25g of diatomaceous earth filter aid.

EXAMPLE E

A 1-liter flask equipped with stirrer, thermowell, powder funnel and Dean-Stark trap was charged with 44.3g of the product of Example .VI and 2c dil oil. To this mixture was added 336g of a poly(isobutene)(molecular weight 1000) substituted succinic anhydride having a saponification number of 100 was added over 0.7 hour at 105° C. N₂ blowing was commenced slowly at 0.35 cfh. This mixture was heated to 160° C. over 1 hour, held at 160° C.-162° C. for 5.5 hours. This mixture was filtered at 150° C. using 30g diatomaceous earth filter aid.

EXAMPLE F

A 1-liter flask equipped with stirrer, thermowell, below surface N₂ inlet and Dean-Stark trap was charged with 50.3g of the product of Example VII and 2c dil oil. To this mixture was added 336g of a poly(isobutene)(molecular weight 1000) substituted succinic anhydride having a saponification number of 100 which was added over 0.9 hour at 110° C. N₂ blowing was commenced slowly at 0.35 cfh. This mixture was heated to 160° C. over 0.6 hour and held at 160°-163° C. for 5.5 hour. This mixture was filtered at 150° C. using 22g of diatomaceous earth filter aid.

EXAMPLE G

A 1-liter flask equipped with stirrer, thermowell, reflux condenser was charged with 224 grams of a poly(isobutene) (molecular weight 1000)- substituted phenol. To the mixture was added 13.2 g. $(CH_2O)_x$'n-butanol 1.6 g. NaOH solution at 72° over 0.15 hr. The mixture was held at 72° C. for 5 hr. (a clear solution was observed after 4.5 hr.). To the mixture was added 25 g. HCl solution to give a neutral solution. To this mixture was added 13.9 grams 1074-27181 over 0.1 hour. The mixture was heated to 110° C. over 1.2 hr. (began removing distillate). The mixture was heated to 120° C. in 0.4 hr. and to 158° C. in 0.6 hr more. The mixture was held at 158°-160° C. for 0.8 hr. The mixture was allowed to stand and held at 160° C. for 5 hr. The mixture was stripped to 160° C. in 30mm. The mixture was filtered at 150° C. using 22g DD 1600. Filtered material is produced.

The foregoing examples illustrate high TBN (45-50) dispersants, which surprisingly exhibit a low free amine content of less than .1 and prepared using the high molecular weight condensed polyamines of the present invention, show better engine test performance than products prepared from more conventional amines, e.g., amine bottoms, tetraethylene amines, and the like. Furthermore, these products give more thermally stable dispersants exhibiting a TBN as high as 77, 40% dilution. However, low TBN dispersants, which exhibit improved performance, may also be prepared according to the present invention.

The above compositions of the invention can be employed in a variety of lubricants based on diverse oils of lubricating viscosity, including natural and synthetic lubricating oils and mixtures thereof These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic transmission fluids, transaxle lubricants, gear lubricants, metal-working lubricants, hydraulic fluids and other lubricating oil and grease compositions can also benefit from the incorporation therein of the compositions of the invention.

Natural oils include animal oils and vegetable oils (e.g., castor, lard oil) liquid petroleum oils and hydrorefined, solvent-treated or acid-treated mineral lubricating oils of the paraffinic, naphthenic and mixed paraffinic-naphthenic types. Oils of lubricating viscosity derived from coal or shale are also useful base oils.

Synthetic lubricating oils include hydrocarbon oils and halo-substituted hydrocarbon oils such as polymerized and interpolymerized olefins [e.g., polybutylenes, polypropylenes, propylene-isobutylene copolymers, chlorinated polybutylenes, poly(1-hexenes), poly(1-octenes), poly(1decenes)]; alkylbenzenes (e.g., dodecylbenzenes, tetradecylbenzenes, dinonylbenzenes, di(2-ethylhexyl)benzenes); polyphenyls (e.g., biphenyis, terphenyls, alkylated polyphenols); and alkylated diphenyl ethers and alkylated diphenyl sulfides and the derivatives, analogs and homologs thereof.

Alkylene oxide polymers and interpolymers and derivatives thereof where the terminal hydroxyl groups have been modified by esterification, etherifications, etc., constitute another class of known synthetic lubricating oils. These are exemplified by polyoxyalkylene polymers prepared by polymerization of ethylene oxide or propylene oxide, the alkyl and aryl ethers of these polyoxyalkylene polymers (e.g., methylpolyisopropylene glycol ether having an average molecular weight of 1000, diphenyl ether of polyethylene glycol having a molecular weight of 500–1000, diethyl ether of polypropylene glycol having a molecular weight of 1000–1500); and mono- and polycarboxylic esters thereof, for example, the acetic acid esters, mixed $C_3$–$C_8$ fatty acid esters and $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monether, propylene glycol). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol ethers such as neopenty-1 glycol, trimethylolpropane, pentaerythritol, dipentaerythritol and tripentaerythritol.

Silicon-based oils such as the polyalkyl-, polyaryl-, polyalkoxy-, or polyaryloxysiloxane oils and silicate oils comprise another useful class of synthetic lubricants; they include tetraethyl silicate, tetraisopropyl silicate, tetra-(2-ethylhexyl) silicate, tetra-(4-methyl-2-ethylhexyl) silicate, tetra-(p-tertbutylphenyl) silicate, hexa-(4-methyl-2-pentoxy)-disiloxane, poly(methyl)siloxanes and poly(methylphenyl) siloxanes. Other synthetic lubricating oils include liquid esters of phosphorus-containing acids (e.g., tricresyl phosphate, trioctyl phosphate, diethyl ester of decylphosphonic acid) and polymeric tetrahydrofurans.

Unrefined, refined and rerefined oils can be used in the lubricants of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques, such as distillation, solvent extraction, acid or base extraction, filtration and percolation are known to those skilled in the art. Rerefined oils are obtained by processes similar to those used to obtain refined oils applied to refined oils which have been already used in service. Such rerefined oils are also known as reclaimed or reprocessed oils and often are additionally processed by techniques for removal of spent additives and oil breakdown products.

Generally the lubricants of the present invention contain a lubricating improving amount of one or more of the compositions of this invention, e.g., sufficient to provide it with improved detergent/dispersant and/or V.I. properties. Normally the amount employed will be about 0.05% to about 20%, preferably about 0.1% to about 10% of the total weight of the lubricating composition. This amount is exclusive of solvent/diluent medium. In lubricating compositions operated under extremely adverse conditions, such as lubricating compositions for marine diesel engines, the metal salts of this invention may be present in amounts of up to about 30% by weight, or more, of the total weight of the lubricating composition.

The invention also contemplates the use of other additives in combination with the compositions of this invention. Such additives include, for example, detergents and dispersants of the ash-producing or ashless type, corrosion- and oxidation-inhibiting agents, pour point depressing agents, extreme pressure agents, antiwear agents, color stabilizers and anti-foam agents.

Many of the above-mentioned extreme pressure agents and corrosion oxidation inhibitors also serve as antiwear agents. Zinc dialkylphosphorodithioates are a well know example.

Pour point depressants are a particularly useful type of additive often included in the lubricating oils described herein. The use of such pour point depressants in oil-based compositions to improve low temperature properties of oil-based compositions is well known in the art. See, for example, page 8 of "Lubricant Additives" by C. V. Smalheer and R. Kennedy Smith (Lezius-Hiles Co., publishers, Cleveland, Ohio, 1967).

Examples of useful pour point depressants are polymethacrylates, polyacrylates; polyacrylamides; condensation products of haloparaffin waxes and aromatic compounds; vinyl carboxylate polymers; and terpolymers of dialkylfumarates, vinylesters- of fatty acids and alkylvinylethers. Pour point depressants useful for the purpose of this invention, techniques for their preparation and their uses are described in U. S. Pat. Nos. 2,387,501; 2,015,748; 2,655,479; 1,815,022; 2,191,498; 2,666,746; 2,721,877; 2,721,878 and 3,250,715 which are hereby incorporated by reference for their relevant disclosures.

Anti-foam agents are used to reduce or prevent the formation of stable foam. Typical anti-foam agents include silicones or organic polymers Additional anti-foam compositions are described in "Foam Control Agents", by Henry T. Kerner (Noyes Data Corporation, 1976), pages 125–162.

The compositions of this invention can be added directly to the the fuels or lubricants. Preferably, however, they are diluted with a substantially inert, normally liquid organic diluent such as mineral oil, naphtha, benzene, toluene or xylene, to form an additive concentrate. These concentrates usually contain from about 10% to 80% by weight of the composition of this invention, and 20% to 90% by weight of the inert diluents. The concentrates also may contain one or more other additives known in the art or described hereinabove.

The fuel compositions of the present invention contain a major proportion of a normally liquid fuel, usually a hydrocarbonaceous petroleum distillate fuel such as motor gasoline as defined by ASTM Specification D439 and diesel fuel or fuel oil as defined by ASTM Specification D396. Normally liquid fuel compositions comprising non-hydrocarbonaceous materials such as alcohols, ethers, organo-nitro compounds and, the like (e,g., methanol, ethanol, diethyl ether, methyl ethyl ether, nitromethane) are also within the scope of this invention as are liquid fuels which are mixtures of one or more hydrocarbonaceous fuels and one or more non-hydrocarbonaceous materials are also contemplated. Examples of such mixtures are combinations of gasoline and ethanol and of diesel fuel and ether. Particularly preferred is gasoline, that is, a mixture of hydrocarbons having an ASTM distillation range from about 60° C. at the 10% distillation point to about 205° C. at the 90% distillation point.

Generally, these fuel compositions contain an amount of the fuel additive of this invention sufficient to improve one or more properties of the fuel such as rust-inhibition, dispersancy, etc.; usually this amount is about 0.005% to about 0.5% by volume, preferably about 0.01% to about 0.1% by volume, based on the volume of such fuel compositions.

The fuel compositions can contain, in addition to the fuel additive compositions of this invention, other additives which are well known to those of skill in the art. These include antiknock agents such as tetraalkyl lead compounds, lead scavengers such as haloalkanes (e.g., ethylene dichloride and ethylene dibromide), deposit preventers or modifiers such as triaryl phosphates, dyes, cetane improvers, antioxidants such as 2,6-di-tertiary-butyl-4methylphenol, rust inhibitors such as alkylated succinic acids and anhydrides, bacteriostatic agents, gum inhibitors, metal deactivators, demulsifiers, upper cylinder lubricants and anti-icing agents.

The fuel additive compositions of this invention can be added directly to the fuel, or they can be diluted with a substantially inert, normally liquid organic diluent such as naphtha, benzene, toluene, xylene or a normally liquid fuel as described above, to form an additive concentrate. These concentrates generally contain from about 20% to about 90% by weight of the composition of this invention and may contain, in addition one or more other conventional additives known in the art or described hereinabove.

The fuel additive compositions of this invention can be provided in concentrate form with less than the above-indicated levels of additives, and then be added directly to the fuel along with additional amounts of the compositions of this invention and other known additives, or be further diluted with additives prior to the addition to the fuel until the level of additives is at the desired level.

What is claimed is:

1. A polyamine comprising units of the formula:

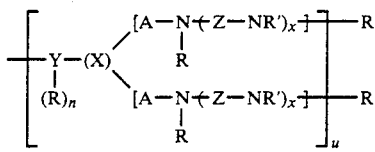

or

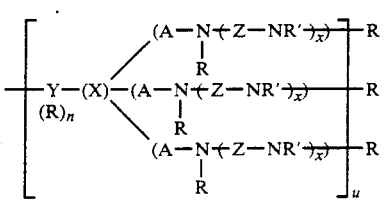

wherein R is independently hydrogen or $C_{1-7}$ hydrocarbyl; R' is hydrogen, alkyl or $NH_2R''(NR'')_y$-, wherein y is a number in the range from 1 to about 6 and R" is an alkylene group of 1 to about 10 carbon atoms; Y represents N or O; X is an alkylene group; A is hydrocarbyl; Z is alkylene of 1 to about 10 carbon atoms or an oxyalkylene of 1 to about 10 carbon atoms; x is a number in the range from 1 to about 10; u is an integer greater than 1; and n is 0 or 1.

2. The polyamine as defined in claim 1 wherein said units comprise:

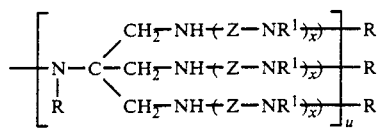

wherein R, $R^1$, Z, x and u are the same as defined in claim 1.

3. The polyamine claimed in claim 1 wherein said polyamine has a viscosity at 100° C. in the range of about 50 cSt to about 200 cSt.

4. A process for making a high molecular weight polyamine composition comprising reacting a mixture comprising (A) at least one compound represented by the formula:

$$(R_{n+1} Y—X_q AOH)_m \qquad (II)$$

wherein each R is independently hydrogen or a hydrocarbyl, Y represents S, N, or O; A and X each independently represent an alkylene group; n is 0 or 1 dependent upon m and q, where q is 0 or 1 and m is 2 or 3; with (B) at least one polyamine represented by the formula:

wherein
each R is hydrogen or a hydrocarbyl group,
each R' is independently hydrogen, alkyl, or $NH_2R''(NR'')_y$-wherein each R" is independently in alkylene group of 1 to about 10 carbon atoms and y is a number in the range of from 1 to about 6,
each Z is independently an alkylene group of 1 to about 10 carbon atoms or an oxyalkylene of 1 to about 10 carbon atoms and
x is a number in the range of from 1 to about 10 in the presence of (C) an acid catalyst at an elevated temperature.

5. The process of claim 4 wherein
reactant (A) is a polyhydric alcohol of formula (II) having 3 hydroxy groups or an amino alcohol of formula (II) having 2 or 3 hydroxy groups and
reactant (B) is an alkylenepolyamine of formula (III) having at least 2 primary nitrogen groups wherein X is an alkylene group of 2 to about 10 carbon atoms.

6. The process of claim 4 wherein reactant (A) is selected from the group consisting of glycerol, trimethylolethane, trimethylolpropane, and tris(hydroxymethyl)aminomethane; and reactant (B) is selected from the group consisting of tetraethylenepentamine, triethylenetetramine, diethylenetriamine, pentaethylenehexamine, and mixtures thereof.

7. The process of claim 4 wherein the polyamine product of the process has a viscosity at 100° C. from about 100% to about 6000% greater than the viscosity of reactant (B).

8. The process of claim 4 wherein reactant (A) is tris(hydroxymethyl)aminomethane.

9. The process of claim 4 wherein the acid catalyst is selected from the group consisting of a mineral acid, an organophosphorus acid, an organosulfonic acid, an alkali or alkaline earth metal partial salt of phosphoric acid, an alkali or alkaline earth metal partial salt of sulfuric acid, $Al_2O_3$, zeolite, triphenylphosphite, and mixtures thereof.

10. The process of claim 4 wherein the acid catalyst is phosphoric acid.

11. The process as defined in claim 4 with the proviso that X and A comprise at least 2 carbon atoms.

12. The process of claim 4 wherein A of Formula (II) of reactant A represents a lower alkylene group and Y represents a nitrogen atom.

13. The process of claim 4 wherein m is 2 or 3.

14. The process of claim 12 wherein m is 2 or 3.

15. The process of claim 1 wherein m is 3.

16. The process of claim 15 wherein polyamine reactant B is an alkylene polyamine selected from at least one of triethylene tetramine, tetraethylenepentamine, pentaethylene-hexamine and mixtures thereof.

17. The process of claim 16 wherein reactant A is tris(hydroxymethyl)aminomethane.

18. The process of claim 17 wherein polyamine reactant B is an alkylene polyamine selected from at least one of triethylene tetramine, tetraethylenepentamine, pentaethylenehexamine and mixtures thereof.

19. The process of claim 17 wherein the polyamine composition is pourable at room temperature and the viscosity of said polyamine composition at 100° C. is at least 100% greater than the viscosity of reactant B.

20. The process of claim 19 wherein the polyamine composition has a viscosity at 100° C. in the range from about 50 cSt to about 200 cSt.

21. The process of claim 13 wherein the acid catalyst is phosphoric acid, an organophosphorus acid, an alkali or alkaline earth metal partial salt of $H_3PO_4$, or triphenylphosphite.

22. The process of claim 21 wherein the acid catalyst is phosphoric acid or an alkali or alkaline earth metal partial salt of $H_3PO_4$.

23. A product produced according to the process of claim 5.

24. A product produced according to the process of claim 6.

25. A product produced according to the process of claim 8.

26. A product produced according to the process of claim 13.

27. A product produced according to the process of claim 14.

28. A product produced according to the process of claim 15.

29. A product produced according to the process of claim 16.

30. A product produced according to the process of claim 19.

31. A product produced according to the process of claim 20.

32. A polyamine compound prepared by reacting a mixture comprising (A) tris(hydroxymethyl)aminomethane and (B) an alkylene polyamine selected from at least one of triethylene tetramine, tetraethylenepentamine, pentaethylenehexamine and mixture thereof.

33. A polyamine compound according to claim 32 having a viscosity at 100° C. in the range of about 50 cSt to about 200 cSt.

34. A lubricating composition comprising a major amount of an oil of lubricating viscosity and a minor amount of at least one polyamine prepared by reacting a mixture comprising (A) a polyhydric alcohol represented by the formula:

$$(R)_2N-(X)-(AOH)_m \qquad (II)$$

wherein each R is independently hydrogen or a hydrocarbyl group; A and X each independently represent an alkylene group; and m is 2 or 3 and (B) an alkylene polyamine selected from at least one of triethylene tetramine, tetraethylenepentamine, pentaethylenehexamine and mixtures thereof.

35. A method for lubricating an internal combustion engine which comprises adding to the engine a lubricant composition as claimed in claim 34.

36. The lubricating composition of claim 34 wherein A and X each comprise not more than one carbon atom.

37. The lubricating composition of claim 34 wherein (A) is tris(hydroxymethyl)-aminomethyl)-aminomethane.

38. A concentrate for formulating a lubricant composition comprising from about 20% to about 90% by weight of a normally liquid, substantially inert, organic solvent/diluent and from about 10% to about 80% by weight of at least one polyamine prepared by reacting a mixture comprising (A) a polyhydric alcohol represented by:

$$(R)_2N-X \ AOH)_m \qquad (II)$$

wherein each R is independently hydrogen or a hydrocarbyl group; A and X each independently represent an alkylene group; and m is 2 or 3 and (B) is an alkylene polyamine selected from at least one of triethylene tetramine, tetraethylenepentamine, pentaethylenehexamine and mixtures thereof.

39. The concentrate of claim 38 wherein A and X each comprise not more than one carbon atom.

40. The concentrate of claim 38 wherein (A) is tris(hydroxymethyl)aminomethane.

* * * * *

UNITED STATES PATENT AND TRADEMARK OFFICE
CERTIFICATE OF CORRECTION

PATENT NO. : 5,053,152
DATED : October 1, 1991
INVENTOR(S) : Thomas F. Steckel

It is certified that error appears in the above—identified patent and that said Letters Patent is hereby corrected as shown below:

Col. 24, line 7, "X" should read --Z--.

Col. 26, lines 2 and 3,
"(A) is tris(hydroxymethyl)-aminomethyl)-aminomethane" should read
--(A) is tris(hydroxymethyl) aminomethane--.

Col. 26, line 8, "$(R)_2$N-X AOH$)_m$" should read

--$(R)_2$ N—(X)—(AOH$)_m$--.

Signed and Sealed this

Twenty-seventh Day of April, 1993

Attest:

MICHAEL K. KIRK

Attesting Officer

Acting Commissioner of Patents and Trademarks